(12) United States Patent
Yamakawa et al.

(10) Patent No.: US 8,176,773 B2
(45) Date of Patent: May 15, 2012

(54) PIEZOELECTRIC SENSOR AND SENSING INSTRUMENT

(75) Inventors: Junichiro Yamakawa, Sayama (JP); Kazuo Akaike, Sayama (JP); Takeru Mutoh, Sayama (JP); Hiroyuki Kukita, Sayama (JP)

(73) Assignee: Nihon Dempa Kogyo Co., Ltd., Tokyo (JP)

( * ) Notice: Subject to any disclaimer, the term of this patent is extended or adjusted under 35 U.S.C. 154(b) by 406 days.

(21) Appl. No.: 12/454,518

(22) Filed: May 19, 2009

(65) Prior Publication Data

US 2009/0288488 A1 Nov. 26, 2009

(30) Foreign Application Priority Data

May 20, 2008 (JP) .................... 2008-131450

(51) Int. Cl.
*G01N 29/036* (2006.01)
*H01L 41/047* (2006.01)

(52) U.S. Cl. ............. 73/61.49; 73/61.79; 73/64.53; 73/579; 310/323.21; 310/366

(58) Field of Classification Search .......... 73/24.01, 73/24.03, 24.06, 61.45, 61.49, 61.75, 61.79, 73/64.53, 579; 310/311, 323.21, 366
See application file for complete search history.

(56) References Cited

U.S. PATENT DOCUMENTS

| 3,266,291 A * | 8/1966 | King, Jr. ............. 73/24.06 |
| 3,329,004 A * | 7/1967 | King, Jr. ............. 73/24.06 |
| 6,544,478 B1 * | 4/2003 | Oyama et al. ........ 422/82.01 |
| 7,036,375 B2 * | 5/2006 | Nozaki ............... 73/579 |
| 2005/0039532 A1 * | 2/2005 | Ohsugi et al. ........ 73/580 |
| 2010/0095751 A1 * | 4/2010 | Kukita et al. ........ 73/64.53 |

FOREIGN PATENT DOCUMENTS

| JP | 2006-003144 | | 1/2006 |
| JP | 2006-033195 | | 2/2006 |
| JP | 2007-108170 | * | 4/2007 |

* cited by examiner

*Primary Examiner* — Daniel Larkin
(74) *Attorney, Agent, or Firm* — Jordan and Hamburg LLP

(57) ABSTRACT

To provide a piezoelectric sensor in which a first electrode for measurement and a second electrode for reference are provided apart from each other on one surface side of a piezoelectric piece and a common electrode is provided on an opposite surface side so as to face the first and second electrodes. A piezoelectric sensor includes: a first electrode for measurement and a second electrode for reference provided apart from each other on one surface side of a piezoelectric piece; a common electrode provided on an opposite surface side of the piezoelectric piece commonly for the first electrode and the second electrode to face the first electrode and the second electrode; and an adsorption layer formed on an area, of the common electrode, to which the first electrode is faced across the piezoelectric piece, to adsorb a substance to be sensed.

4 Claims, 14 Drawing Sheets

Fig. 10
(a)
PRIOR ART
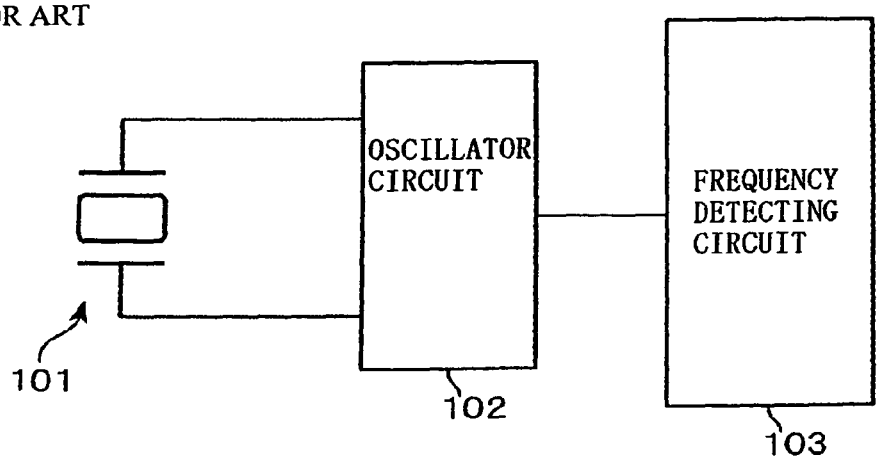
(b)
PRIOR ART
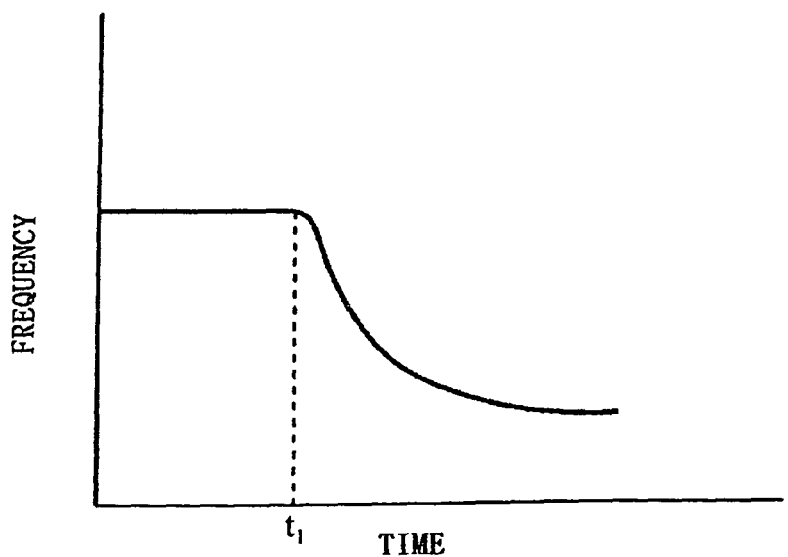

PIEZOELECTRIC SENSOR AND SENSING INSTRUMENT

BACKGROUND OF THE INVENTION

1. Field of the Invention

The present invention relates to a piezoelectric sensor which senses a substance to be sensed in a sample fluid based on a change in natural frequency of a piezoelectric piece by making an adsorption layer formed on an electrode provided on the piezoelectric piece adsorb the substance to be sensed, and to a sensing instrument sensing a substance to be sensed by using the piezoelectric sensor.

2. Description of the Related Art

As an instrument for sensing a trace substance in a solution or gas, there has been known a sensing instrument which uses QCM (Quartz Crystal Microbalance) formed by a quartz resonator which is a piezoelectric resonator mainly formed by an AT-cut crystal piece as a quartz piece. A sensing instrument of this type senses a trace substance by making the quartz resonator included in a quartz oscillator circuit adsorb the trace substance and detecting a change in its oscillation frequency (resonant frequency). Examples of the trace substance are dioxin which is an environmental pollutant, a specific antigen in blood or serum, and so on, and the sensing instrument senses an extremely low concentration, for example, on ppb to ppt level, of these substances.

FIG. 10(a) shows an example of the structure of such a sensing instrument, in which 101, 102 denote a quartz resonator and an oscillator circuit forming a quartz oscillator circuit respectively. Further, on a subsequent stage of the oscillator circuit 102, a frequency detecting circuit 103 is connected to detect a change in oscillation frequency of the quartz resonator 101. One surface side of the quartz resonator 101 is in contact with an airtight space and the other surface side thereof is in contact with a measurement atmosphere to which a sample solution containing a substance to be sensed is supplied. An adsorption layer is formed on a front surface, which is the other surface side, to adsorb the substance to be sensed. At time t1 shown in FIG. 10(b), the sample solution is supplied to the quartz resonator 101, and when the substance to be sensed is adsorbed, the oscillation frequency of the quartz resonator 101 lowers due to a mass load effect. Based on the frequency change, the substance to be sensed in the sample solution is detected or the concentration thereof is measured.

However, the oscillation frequency of the quartz resonator 101 sometimes changes by factors other than the adsorption of the substance to be sensed. A possible factor may be the influence of the vibration given to the quartz resonator, for example, when a person walks in a room in which the sensing instrument is installed, but especially because the frequency of the quartz resonator changes depending on the temperature, there is a concern that the frequency may be influenced by a temperature change of a measurement environment due to an air conditioner, weather, and the like. When such a frequency change is caused by such a factor other than the adsorption of the substance to be sensed, measurement accuracy lowers, which as a result may possibly cause cases where, for example, the determination result becomes "equal to or lower than tolerable concentration" even though a toxic substance whose concentration is over a tolerable range is contained in a river, or the determination result becomes "present" even though a cancer marker is not present in blood, and the incorrect recognition causes a crucial situation.

Therefore, some sensing instrument has the structure shown in FIG. 11. 104A and 104B denote quartz resonators similar to the quartz resonator 101, but the quartz resonator 104A does not have the adsorption layer and is structured as a quartz resonator for reference not adsorbing a substance to be sensed. By changing a switch 106, oscillation outputs of the quartz resonators 104A, 104B are output to a frequency detecting circuit 103 in a time-division manner. Then, an arithmetic part 107 connected to the frequency detecting circuit 103 creates time-series data F1, F2 of the oscillation frequencies of the quartz resonators 104A, 104B detected by the detecting circuit 103, and further calculates a difference between F1 and F2 to create time-series data F1-F2. That is, since a frequency change ascribable to a temperature change is reflected in the time-series data F1 and a frequency change ascribable to the adsorption of the substance to be sensed and the temperature change is reflected in the time-series data F2, the time-series data F1-F2 corresponding to a difference therebetween represent the frequency change in which the influence of the temperature change is cancelled and which is thus caused only by the adsorption of the substance to be sensed. Therefore, the use of the time-series data F1-F2 as a basis of the detection of the substance to be sensed enables improved measurement accuracy.

Incidentally, in order to more improve the measurement accuracy by realizing higher frequency stability against temperature, it has been considered to structure a quartz oscillator circuit by using a quartz resonator in which two vibration areas are set on one quartz piece and excitation electrodes are formed on the quartz piece so as to correspond to the respective vibration areas, and to detect the influences of both the adsorption of the substance to be sensed and the temperature change in a vibration part including one of the vibration areas and detect only the influence of the temperature change in a vibration part including the other vibration area, as in the aforesaid sensing instrument in FIG. 11. That is, in this example, the single quartz piece functions as two quartz resonators and the vibration areas are formed on the common quartz piece, and therefore, it is possible to obtain frequency-temperature characteristics in which variations of the oscillation frequencies output from the respective vibration areas when an ambient temperature changes are substantially equal. Then, based on the difference between the time-series data F1, F2 which are obtained from the respective vibration areas as in the aforesaid sensing instrument in FIG. 11, a substance to be sensed is detected. Patent documents 1, 2 describe such a quartz oscillator circuit.

FIG. 12 shows a quartz oscillator circuit 110 including a quartz piece 111 as structured above. 112, 113 in FIG. 12 denote excitation electrodes corresponding to a first vibration area 114 and a second vibration area 115 of the quartz piece 111 respectively. 116 in FIG. 12 denotes a common excitation electrode commonly used for the vibration areas 114, 115. 117 denotes the aforesaid quartz resonator, which includes: the first vibration area 114 including the quartz piece 111 and the electrodes 112, 116; and the second vibration area 115 including the quartz piece 111 and the electrodes 113, 116. The first vibration area 114 and the second vibration area 115 are structured to vibrate independently of each other, the former being vibrated by the electrodes 112, 116 and the latter being vibrated by the electrodes 113, 116.

Since, on a microscopic level, the first vibration area 114 and the second vibration area 115 are different in thickness and the electrodes 112, 113 are different in thickness, frequencies of the first vibration area 114 and the second vibration area 115 are slightly different, the difference therebetween being, for example, on a several ten kHz order in a case of a 9 MHz quartz resonator. If their frequencies are thus extremely close to each other, they are attracted to each other, resulting in frequency signals with low Q values. Therefore, the electrodes 112, 113 are made slightly different in thickness so that the frequencies differ slightly. 123, 124 denote a set of two Colpitts oscillator circuits serially connected to the quartz resonator 117 in order to take out the oscillation frequencies by using the vibration areas 114, 115.

FIG. 13 is a side view of the quartz resonator 117, in which 119 denotes a board, 122 denotes an airtight space in contact with a rear surface of the quartz resonator 117, and 120 denotes an adsorption layer adsorbing a substance to be sensed contained in a sample solution 118 supplied to a front surface of the quartz resonator 117.

Incidentally, in the sensing instrument including the quartz oscillator circuit 110, a frequency difference of one of the vibration areas is corrected by the frequency difference of the other vibration area to remove the influence of the temperature characteristic, whereby only a variation of the frequency ascribable to the adsorption of the substance to be sensed is extracted, as described above. Therefore, it is necessary to vibrate the two vibration areas 114, 115 independently of each other. Therefore, when the quartz resonator 117 is structured as having the two vibration areas 114, 115 on the single quartz piece 111 as described above, it is necessary to reduce the mutual influence of the vibration between the vibration areas 114, 115. However, as shown in FIG. 13, when the quartz resonator 117 in contact with the sample solution 118 is seen from an electrical point of view, the excitation electrode 112 of the vibration area 114 and the excitation electrode 113 of the other vibration area 115 are connected to each other via a low-resistance component 121 shown by the dotted line in FIG. 13, due to the impedance of the sample solution 118 itself. FIG. 14 is a Smith chart showing the measurement result of the resistance component 121, and as is seen in the Smith chart, when the quartz oscillator circuit 110 uses a frequency of, for example, 9.125 MHz, the impedance is about 100 Ω.

The presence of such a resistance component 121 affects the oscillations of the oscillator circuits 123, 124, and it becomes difficult to maintain the oscillations of the vibration areas 114, 115, leading to a failure in the measurement, or an unnecessary component generated by the influence that the vibration of one of the vibration areas gives to the vibration of the other vibration area is output in the frequency signal taken out from each of the vibration areas, leading to a difficulty in highly reliable measurement.

[Patent Document 1]

Japanese Patent Application Laid-open No. 2006-33195: claim 1, paragraph 0012 to paragraph 0014, paragraph 0018 to paragraph 0019, FIG. 1, FIG. 4

[Patent Document 2]

Japanese Patent Application Laid-open No. 2006-3144, paragraph 0015, paragraph 0023, FIG. 2

SUMMARY OF THE INVENTION

The present invention was made under such circumstances and has an object to provide a piezoelectric sensor in which a first electrode for measurement and a second electrode for reference are provided apart from each other on one surface side of a piezoelectric piece and a common electrode is provided on the opposite surface side so as to face the first and second electrodes, and which achieves highly reliable oscillation by reducing the influence of electrical coupling between the first electrode and the second electrode. Another object is to provide a sensing instrument that uses the piezoelectric sensor to be capable of highly reliable measurement.

A piezoelectric sensor sensing a substance to be sensed in a sample fluid based on a change in natural frequency of a piezoelectric piece by making an adsorption layer formed on an electrode provided on the piezoelectric piece adsorb the substance to be sensed, the piezoelectric sensor comprising:

a first electrode for measurement and a second electrode for reference provided apart from each other on one surface side of the piezoelectric piece, a common electrode provided on an opposite surface side of the piezoelectric piece commonly for said first electrode and said second electrode to face said first electrode and said second electrode, an adsorption layer formed on an area, of said common electrode, to which said first electrode is faced across the piezoelectric piece, to adsorb the substance to be sensed, and connecting mutually the area of said common electrode to which said first electrode is faced across the piezoelectric piece and an area of said common electrode to which said second electrode is faced across the piezoelectric piece electrically so that these areas are same electric potential.

The piezoelectric sensor may further include a support member supporting the piezoelectric piece, and the first electrode and the second electrode may be located in a closed space formed by a recessed portion of the support member.

A sensing instrument of the present invention includes:

the above-described piezoelectric sensor;

a first oscillator circuit connected between the first electrode and the common electrode to vibrate a vibration area between the first electrode and the common electrode in the piezoelectric piece; and a second oscillator circuit connected between the second electrode and the common electrode to vibrate a vibration area between the second electrode and the common electrode in the piezoelectric piece, wherein the common electrode is grounded.

The piezoelectric sensor of the present invention includes: the first electrode for measurement and the second electrode for reference which are provided on the one surface side of the piezoelectric piece apart from each other; the common electrode provided on the opposite surface side of the piezoelectric piece commonly for the first electrode and the second electrode to face the first electrode and the second electrode; and the adsorption layer formed on the area, of the common electrode, to which the first electrode is faced, to adsorb the substance to be sensed in the sample fluid. Therefore, it is possible to prevent the first electrode and the second electrode from being electrically connected to each other via the sample fluid due to the contact of the first electrode and the second electrode with the sample fluid, resulting in a highly reliable oscillation operation of the piezoelectric piece. Therefore, applying the piezoelectric sensor to the sensing instrument realizes highly reliable detection of a substance to be sensed.

BRIEF DESCRIPTION OF THE DRAWINGS

FIG. 10(a) and FIG. 10(b) are a block diagram of a conventional sensing instrument;

DETAILED DESCRIPTION OF THE PREFERRED EMBODIMENTS (First Embodiment)

Figure 1:
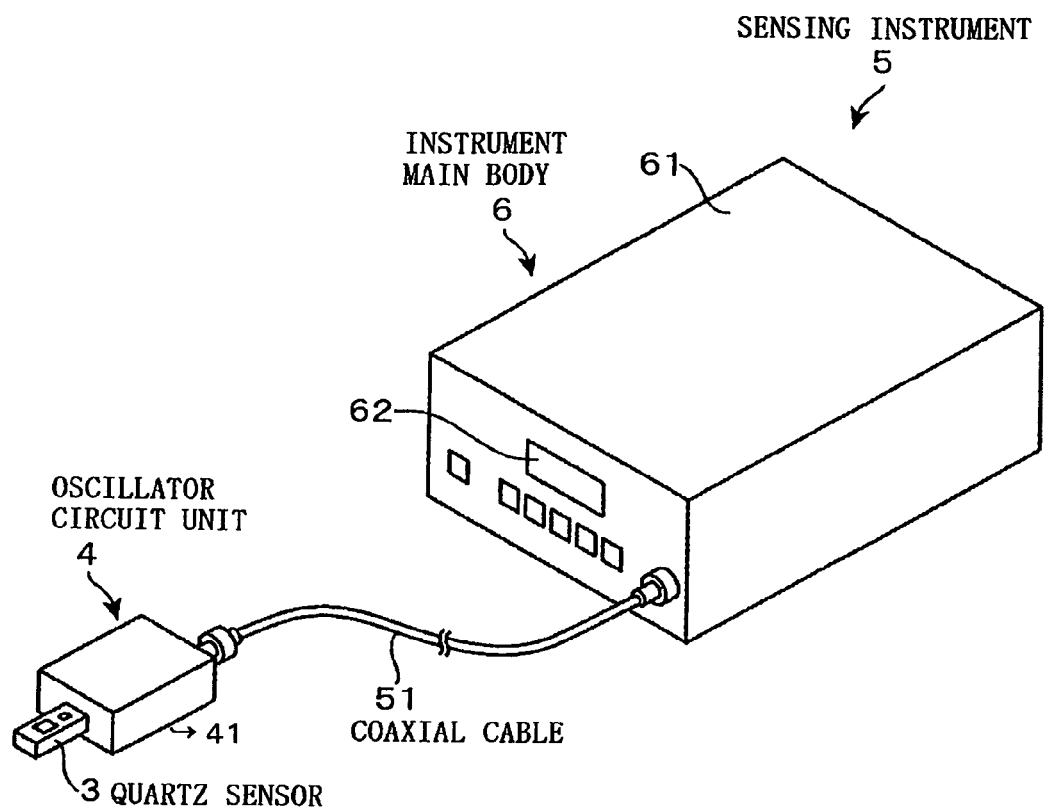
FIG. 1 is a view showing an exterior structure of a sensing instrument according to an embodiment.

Hereinafter, a sensing instrument 5 having a function of sensing a specific antigen in, for example, blood or serum will be described as a sensing instrument including a quartz resonator as a piezoelectric resonator according to this embodiment. As shown in the exterior structure view in FIG. 1, the sensing instrument 5 includes an oscillator circuit unit 4 and an instrument main body 6, and the oscillator circuit unit 4 is attachably/detachably connected to the instrument main body 6 via a cable, for example, a coaxial cable 51. A display part 62 provided on a front surface of a casing 61 of the instrument main body 6 plays a role of displaying the measurement result of, for example, a frequency, a variation of the frequency, or the like, and is formed by, for example, a LED display screen or a liquid crystal display screen.

Figure 2:
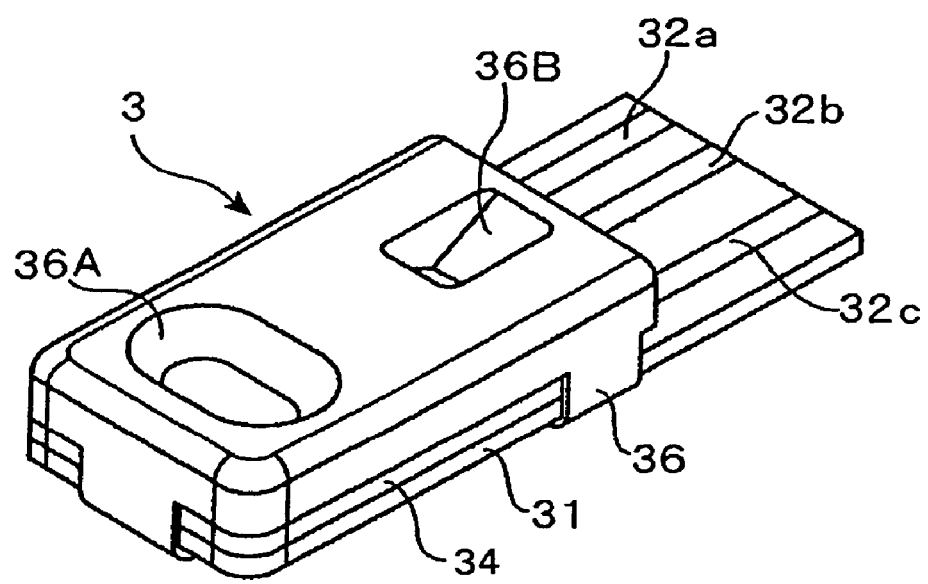
FIG. 2 is a view showing an exterior view of a quartz sensor connected to the sensing instrument.
Figure 3:
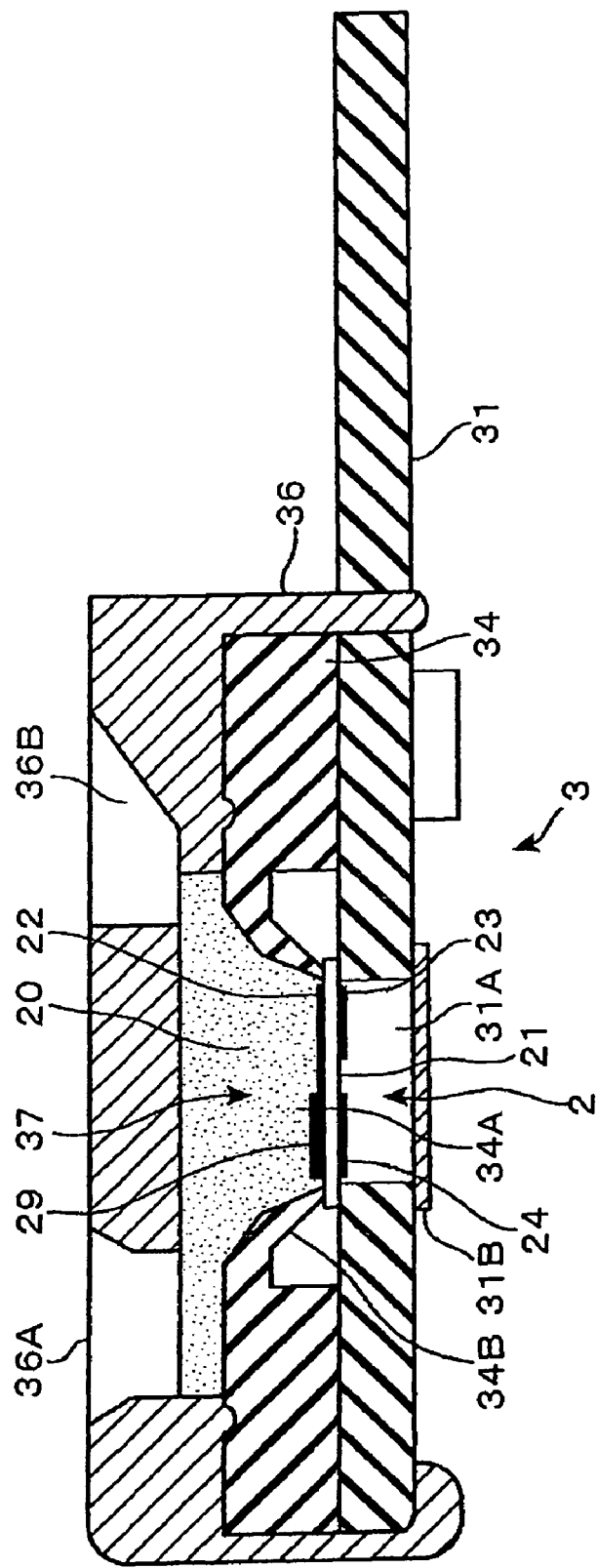
FIG. 3 is a vertical sectional view of the quartz sensor.

A quartz sensor 3, whose exterior structure is shown in FIG. 2 and whose vertical cross section is shown in FIG. 3, is attachably/detachably connected to the oscillator circuit unit 4. As will be described later, the quartz sensor 3 forms a quartz oscillator circuit 40 which is a piezoelectric oscillator circuit, and includes a quartz resonator 2. The quartz resonator 2 includes: a quartz piece 21 which is, for example, an AT-cut circular piezoelectric piece; and electrodes 22, 23, 24 made of, for example, gold.

Figure 4:
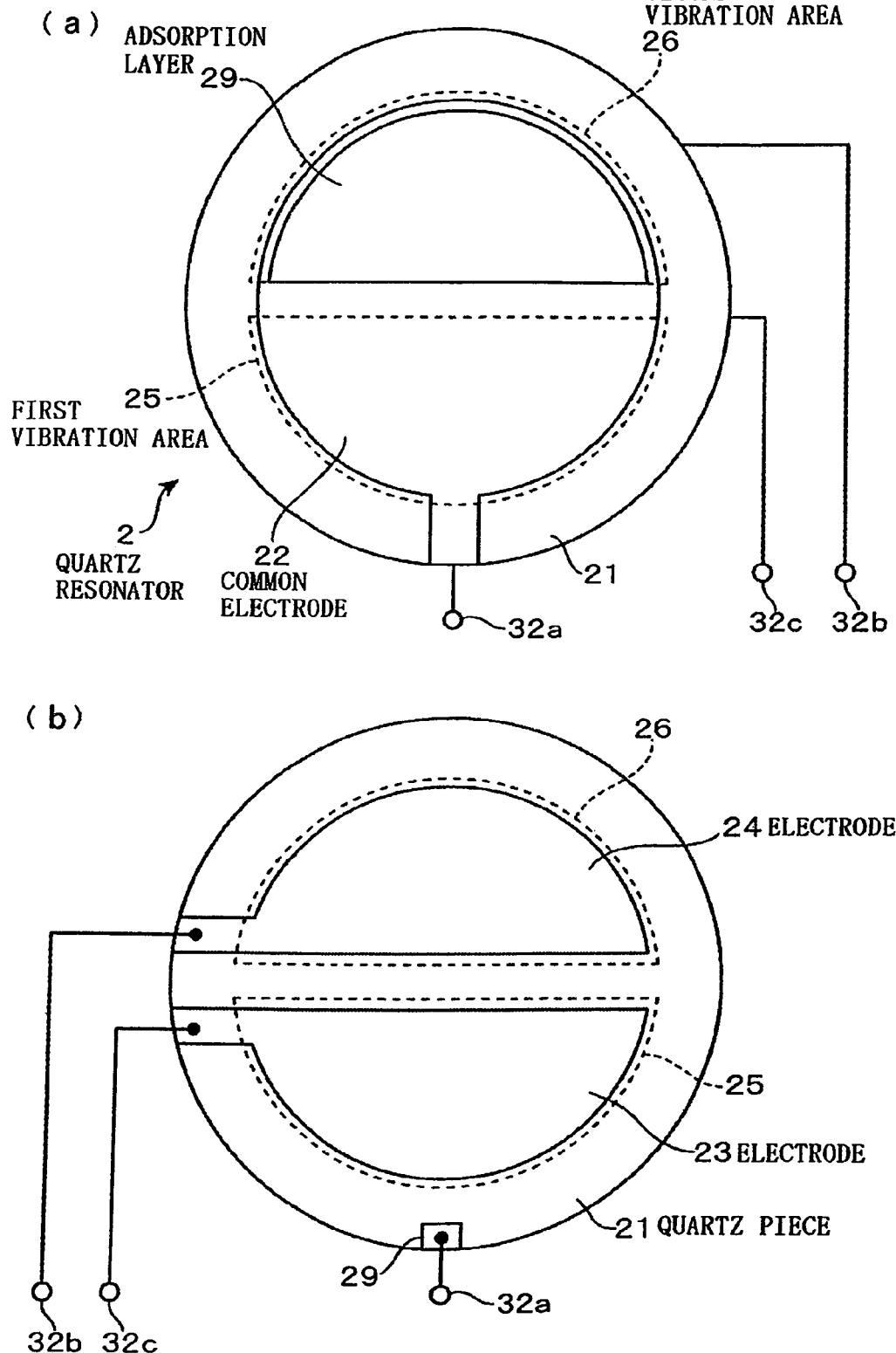
FIG. 4(*a*) and FIG. 4(*b*) are plane views of a quartz resonator assembled in the quartz sensor.

FIG. 4(a) and FIG. 4(b) show a front surface and a rear surface of the quartz resonator 2 respectively. On the front surface of the quartz resonator 2, a circular common electrode 22 commonly used for later-described vibration areas is formed. On the rear surface of the quartz resonator 2, an electrode 23 for reference and an electrode 24 for measurement are formed apart from each other, and the electrodes 23, 24 are formed in semicircles to which one circle is divided along the diameter of the quartz piece 21, for instance. A part of a periphery of the electrode 22 is led out of the quartz piece 21 to enter the rear surface of the quartz piece 21, and when the piezoelectric resonator 2 is placed on a later-described board 31, this entering part comes into contact with an electrode formed on the board 31 to be electrically connected thereto. Further, parts of peripheries of the electrodes 23, 24 are led out of the quartz piece 21 and the led-out parts come into contact with other electrodes formed on the board 31 to be electrically connected thereto.

The electrodes 23, 24 face the electrode 22, and in the quartz piece 21, an area between the electrode 23 and the common electrode 22 is a first vibration area 25 and an area between the electrode 24 and the electrode 22 is a second vibration area 26. The common electrode 22 is used commonly for the vibration areas 25, 26, and the first vibration area 25 and the second vibration area 26 are vibrated independently of each other, the former being vibrated by the electrodes 22, 23 and the latter being vibrated by the electrodes 22, 24, and can output frequency signals. As is described in "DESCRIPTION OF THE RELATED ART", the electrodes 22, 23 are slightly different in thickness so that their oscillation frequencies in a major mode differ by 50 kHz, for instance, without departing from the purpose of equalizing their frequency-temperature characteristics. Hereinafter, an output from the first vibration area 25 will be referred to as a channel 1 and an output from the second vibration area 26 will be referred to as a channel 2.

Figure 5:
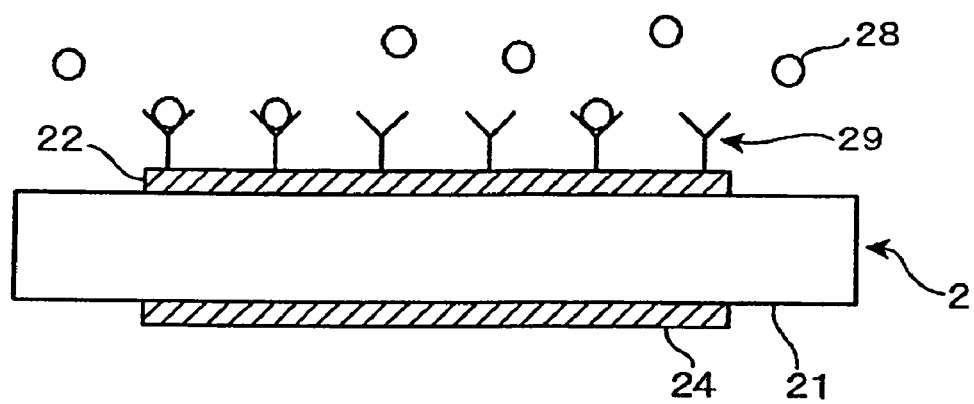
FIG. 5 is an explanatory view showing the mechanism for sensing an antigen by the quartz resonator.

On a front surface of the common electrode 22, provided is an adsorption layer (reaction film) 29 made of an antibody selectively reacting with and binding to a substance to be sensed 28 which is an antigen, as shown in FIG. 4(a) and FIG. 5. The adsorption layer 29 is formed on an area, of the front surface of the common electrode 22, to which the electrode 24 of the second vibration area 26 is faced, and a second oscillation frequency F2 of the second vibration area 26 can be changed by utilizing a mass load effect when the substance to be sensed 28 is adsorbed by the adsorption layer 29 by the antigen-antibody reaction. As a result, it is possible to take out, from the second channel 2, an oscillation frequency F2 which is obtained after the second oscillation frequency F2 is influenced by both the adsorption of the antibody and a temperature change. On the other hand, since the adsorption of the substance to be sensed 28 does not occur in the first vibration area 25, it is possible to take out, from the first channel 1, an oscillation frequency F1' which is obtained after a first frequency F1 is influenced only by the temperature change. It should be noted that the adsorption layer 29 may come off the edge of the facing area, provided that it is formed on the facing area, unless the aforesaid purpose of extracting, from the first vibration area, the frequency change influenced by the temperature change and extracting, from the second vibration area, the frequency change influenced both by the temperature change and the adsorption of the antibody is hindered.

Incidentally, a block layer made of an antibody (protein) not reacting with the substance to be sensed 28 contained in a sample solution may be provided on an area, of the electrode 22, where the adsorption layer 29 is not formed, thereby more surely preventing a change in the first oscillation frequency F1. Further, when the adsorption layer 29 is an antibody for capturing an antigen which is a substance to be sensed in the sample solution, the block layer may be formed by supplying the electrode 22 with a liquid containing protein not reacting with the antigen and making the protein adhere onto the electrode 22. Such a process causes the protein forming the block layer to adhere also between an antibody group forming the adsorption layer 29 on the electrode 22. As a result, it is possible to inhibit other components such as antigens other than the substance to be sensed in the sample solution, for example, blood or serum from adhering onto the electrode 22, which enables more accurate measurement.

Returning to FIG. 2 and FIG. 3, the structure of the quartz sensor 3 as the piezoelectric sensor will be described. The quartz sensor 3 includes the board 31 as a support member in whose center portion a through hole 31A slightly smaller in diameter than the quartz resonator 2 is formed, the quartz resonator 2, a rubber sheet 34, in whose center portion a circular through hole 34A is formed, and an upper cover case 36. On a rear surface side of the board 31, a sheet 31B is provided to close the through hole 31A, and a recessed portion is formed by the board 31 and the sheet 31B. Further, the quartz resonator 2 is provided so as to close the through hole 31A from a front surface side of the board 31, and the rubber sheet 34 is stacked on the board 31 so that a pressing part 34B forming a sidewall of the through hole 34A presses a peripheral edge portion of the quartz resonator 2 to an outer peripheral portion of the through hole 31A of the board 31, and the upper cover case 36 is further mounted from above the rubber sheet 34. By such a structure, a space formed by the through hole 31A and the sheet 31B becomes a closed airtight space, and a rear surface side of the quartz resonator 2 comes into contact with the airtight space, so that a Languban-typed quartz sensor is formed, and the electrodes 22, 23, 24 of the quartz resonator 2 are electrically connected to connection terminals 32a, 32c, 32b, which are the electrodes formed to extend toward one end side of the printed circuit board 31.

Figure 6:
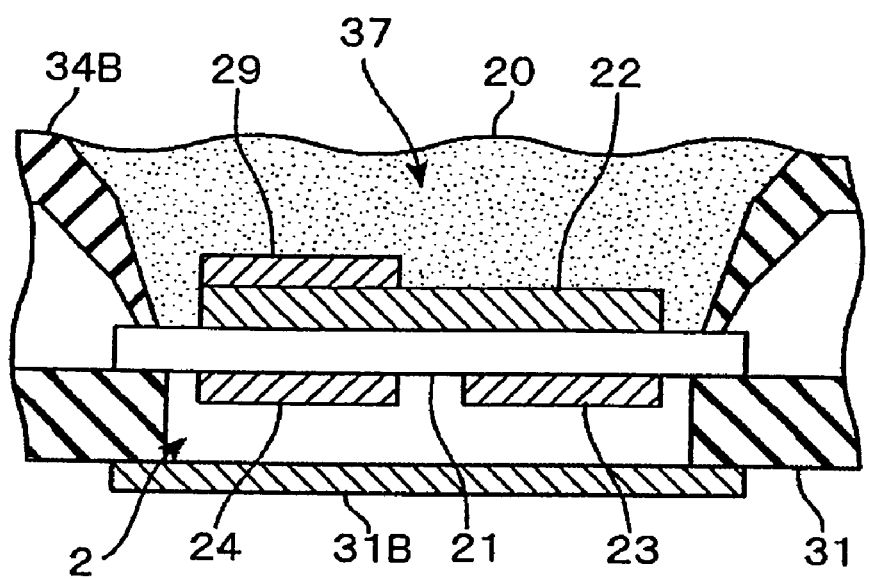
FIG. 6 is a side view of the quartz resonator immersed in a sample solution.

In the upper cover case 36, an injection port 36A of the sample solution 20 and a check port 36B for confirmation that the sample solution 20 has been injected are provided. As shown in FIG. 6, when the sample solution 20 is injected from the injection port 36A, it is possible to fill the sample solution 20 in a space 37 on a front surface side of the quartz resonator 2, which is formed by the through hole 34A, so that the electrode 22 of the quartz resonator 2 is immersed in the sample solution 20.

Figure 7:
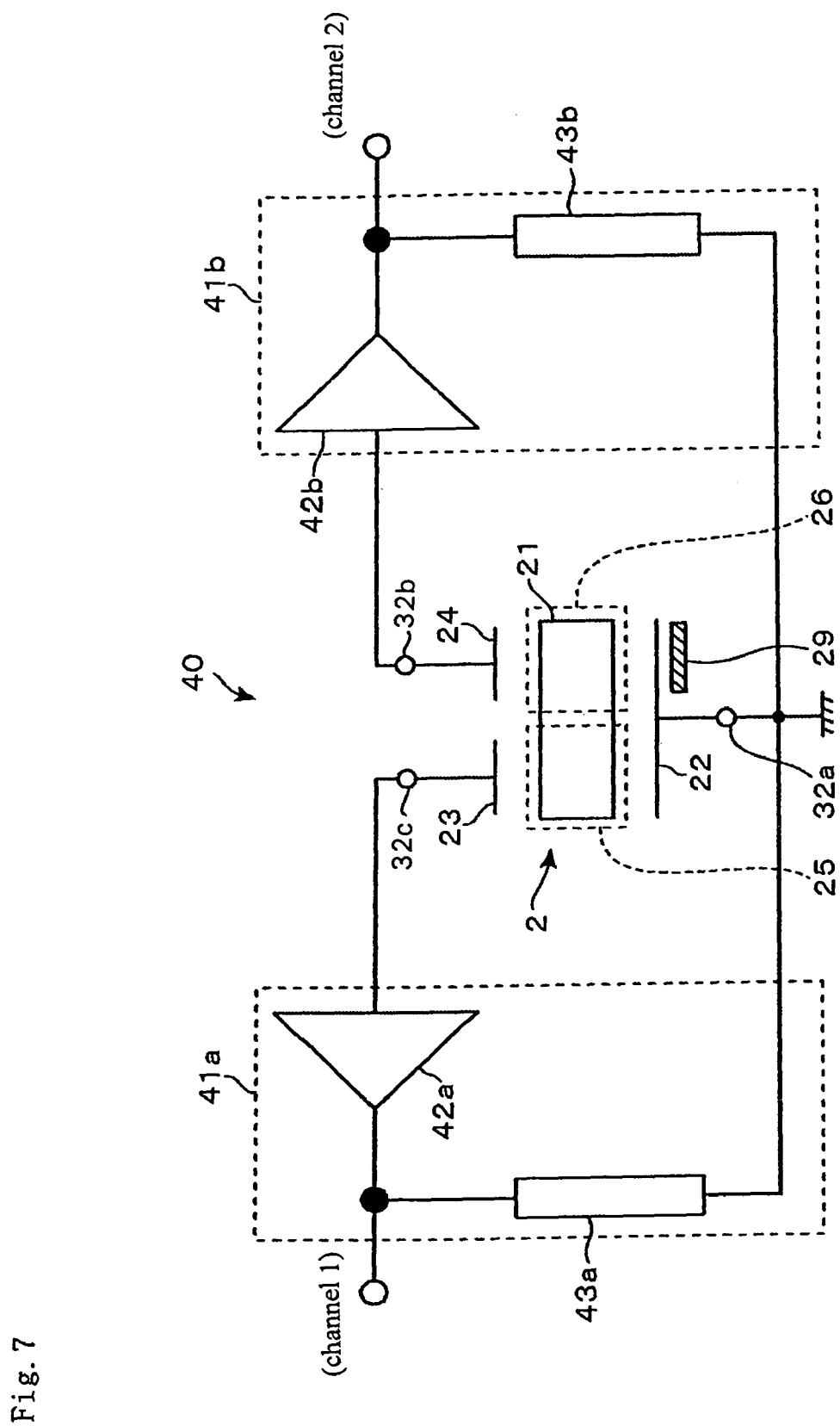
FIG. 7 is a circuit diagram showing a structure example of a quartz oscillator circuit.

The quartz sensor 3 including the quartz resonator 2 described above is connected to a casing 41 of the oscillator circuit unit 4 to form the quartz oscillator circuit 40. As shown in the rough block diagram in FIG. 7, the quartz oscillator circuit 40 is capable of outputting frequency signals having a first and a second oscillation frequency corresponding to the vibrations of the first and second vibration areas 25, 26 when the electrodes 23, 24 of the quartz resonator 2 are connected to a first and a second oscillator circuit (amplifier) 41a, 41b. Further, in the quartz oscillator circuit 40, the common electrode 22 is grounded. 42a, 42b in FIG. 7 denote transistors included in the oscillator circuits 41a, 41b, and 43a, 43b in FIG. 7 denote capacitors included in the oscillator circuits 41a, 41b.

Here, since the first vibration area 25 and the second vibration area 26 provided in the quartz resonator 2 are immersed in the common sample solution 20 in the same quartz sensor 3, temperature conditions where the areas 25, 26 are put are substantially the same. Further, since the areas 25, 26 are provided on the common quartz piece 2, the first oscillation frequency F1 and the second oscillation frequency F2 exhibit substantially the same frequency-temperature characteristic. In the quartz resonator 2, the rear surface side where the two electrodes 23, 24 are formed faces the airtight space, and in the quartz resonator 2, only the common electrode 22 formed on the front surface side is in contact with the sample solution 20. Therefore, the sample solution 20 does not work as an impedance component between the electrodes 23, 24 unlike in the DESCRIPTION OF RELATED ART, and thus the electrodes 23, 24 are electrically isolated, which makes it possible for the vibration areas 25, 26 to be independently and stably oscillated. From the vibration areas 25, 26, the frequency signals corresponding to their frequencies are extracted to be output from the respective channels, without being attracted to each other even though being close to each other and thus with high Q values.

Figure 8:
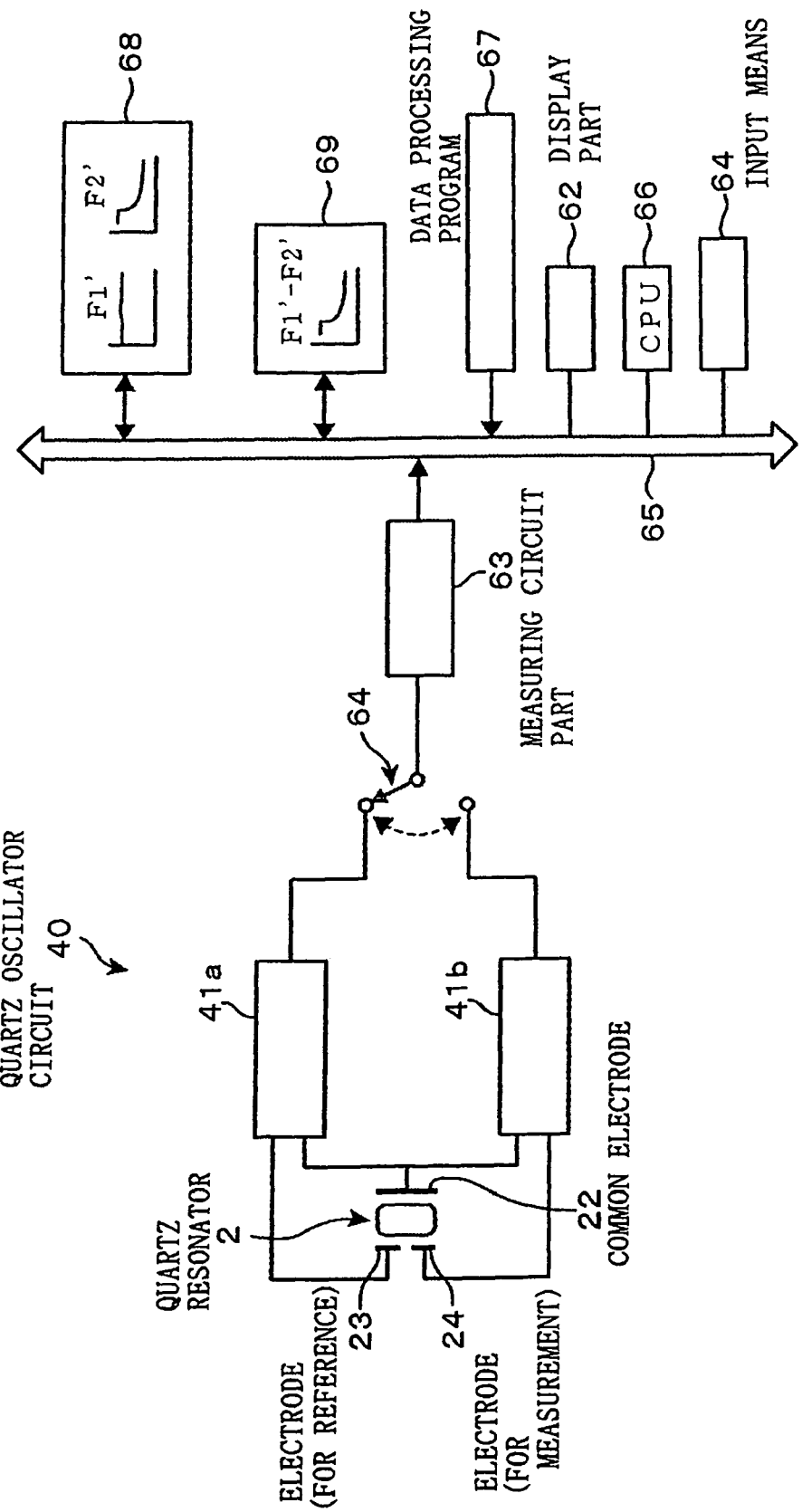
FIG. 8 is a block diagram of the sensing instrument.

FIG. 8 is a block diagram of the sensing instrument 5. As is previously described, the quartz resonator 2 in the quartz sensor 3 and the oscillator circuits 41a, 41b in the oscillator circuit unit 4 form the quartz oscillator circuit 40, and the quartz oscillator circuit 40 is connected to the instrument main body 6. In the instrument main body 6, a measuring circuit part 63 is provided in a connection part with the quartz oscillator circuit 40. In this example, the measuring circuit part 63 functions to digitally process the frequency signals, which are input signals, to measure the oscillation frequencies of the respective channels.

Further, on a previous stage of the measuring circuit part 63, a switch part 64 is provided to successively let the output signals from the respective channels into the measuring circuit part 63. The switch part 64 functions to take out the frequency signals from the two oscillator circuits 41a, 41b in a time-division manner, which enables one to find the oscillation frequencies of the respective channels in parallel. For example, one second is divided by n (n is an even number) and the oscillation frequency of each of the channels is successively found by a 1/n second process. This means that the frequencies are obtained at least once or more in one second even though the frequencies are not measured completely simultaneously in a strict sense. Therefore, it is possible to obtain the frequencies of the respective channels substantially simultaneously.

The instrument main body 6 includes a data bus 65, to which a CPU (central processing unit) 66, a storage storing a data processing program 67, a first memory 68, a second memory 69, and the aforesaid measuring circuit part 63 are connected. Further, the aforesaid display part 62 such as a monitor and an input means 64 such as a keyboard are connected to the data bus 65, and a personal computer and so on, not shown in FIG. 8, are connected to the instrument main body 6.

The data processing program 67 functions to obtain time-series data relating to the oscillation frequencies of the respective channels based on signals output from the measuring circuit part 63 and store the time-series data in the first memory 68. Along with the data obtaining operation, the data processing program 67 has a function of calculating differences F1'- F2' between the time-series data of the oscillation frequency F1' and the oscillation frequency F2' which are obtained in the same time zone from the channel 1 and the channel 2 respectively, thereby obtaining time-series data of the difference data and storing the time-series data in the second memory 69. Further, these data can be displayed on the display part 62 according to the selection by a user. The CPU 66, the data processing program 67, and the memories 68, 69 realizing these functions form a means for measuring a variation of the oscillation frequency.

Next, the operation of the sensing instrument 5 having the above-described structure will be described, taking as an example a method of finding the concentration of some kind of antigen in blood or serum. When the instrument main body 6 is first activated and the quartz sensor 3 is inserted to an insertion port of the oscillator circuit unit 4, the vibration areas 25, 26 start oscillating. From the electrodes 23, 24 provided in the vibration areas 25, 26 respectively, the frequency signals corresponding to the frequencies thereof are taken out and are output from the respective channels. Then, these frequency signals are taken into the measuring circuit part 63 in a time-division manner, and after the frequency signals are A/D-converted, digital values thereof are subjected to signal processing. Then, the aforesaid frequencies F1', F2' are extracted from the frequency signals of the two channels and these frequencies are stored in the first memory 68 substantially simultaneously (for example, at a time interval of ½ second), and this operation is continued.

Next, when the user injects, for example, salt water as a diluting liquid to the quartz sensor 3, an environmental atmosphere of the vibration areas 25, 26 of the quartz resonator 2 changes from a vapor phase to a liquid phase, so that the frequencies of the respective channels become lower. Meanwhile, serum taken from a human body is diluted by a diluting liquid, for example, salt water to 100 times, to prepare the sample solution. Then, the sample solution is injected into the quartz sensor 3. As a result, when an antigen-antibody reaction progresses in the second vibration area 26 on which the adsorption layer (reaction film) 29 is formed, the frequency F2' further lowers due to the mass load effect. On the other hand, the frequency F1' which changes according to the temperature of the sample solution is output from the channel 1 on the first vibration area 25 side. As described above, even when the quartz resonator 2 is thus immersed in the sample solution, the rear surface where the two electrodes 23, 24 are formed is not in contact with the sample solution, which prevents the electrodes 23, 24 from being electrically coupled due to the impedance of the sample solution itself.

The time-series data of the frequencies thus output from the respective channels are stored in the first memory 68, and the difference between the frequency F2' of the channel 2 and the frequency F1' of the channel 1 is also calculated, and the time-series data of the difference therebetween are stored in the second memory 69. The difference frequency may be found at a timing while the frequencies of the respective channels are successively obtained. An example of a possible method is such that, after the frequency F1' of the channel 1 is obtained and then the frequency F2' of the channel 2 is obtained, F2' is subtracted from F1' and the difference therebetween is written to the second memory 69. A possible alternative method is such that, after the time-series data of the frequencies of the respective channels are obtained, the differences are calculated, with the time axes of these data being aligned, and the time-series data of the difference is created.

Subsequently, when, for example, the user selects a command for displaying the difference data of the channels by using the input means 64, the selected difference data out of the time-series data in the second memory 68 is displayed on the display part 62 as a graph. Even if the ambient temperature changes in the process of such a series of operations to cause a change in the frequencies F1', F2' from the respective channels, this temperature change occurs to the common quartz resonator 2 under the same condition. Therefore, taking the difference between the frequencies cancels the influence of the temperature change, and therefore, the decrease in the frequency in the difference data stored in the second memory 69 can be said to be ascribable only to the adsorption of the antigen by the quartz piece 21. Further, a fluctuating factor removable by using the quartz oscillator circuit 40 is not limited to the temperature change, but this removal is also effective, for example, when external vibration is applied, when viscosity of the sample solution (blood or serum) changes, and the like.

Based on a variation of the difference data thus displayed, the user is capable of finding the concentration of the substance to be sensed by using a pre-found relational expression (calibration curve) between a variation of the oscillation frequency and the concentration of the substance to be sensed. Here, the decision of a variation of the difference data and the decision of the concentration of the substance to be sensed using the calibration curve may be performed in the sensing instrument 5, or may be performed by the user reading the data displayed on, for example, the display part 62.

According to the quartz sensor 3 of the present invention, the electrodes 23, 24 provided in the first vibration area 25 and the second vibration area 26 in the quartz resonator 2 respectively to excite the vibration areas 25, 26 are both in contact with the airtight space, and only the common electrode 22 provided commonly for the vibration areas 25, 26 to excite the vibration areas 25, 26 is in contact with the sample solution. This prevents the coupling of the electrodes 23, 24 due to the impedance of the sample solution, so that the first vibration area 25 and the second vibration area 26 are electrically isolated from each other and thus are less influenced by each other, which results in a highly reliable oscillation operation of the first and second vibration areas 25, 26. Therefore, in the quartz oscillator circuit 40, the output of an unnecessary component generated when one of the vibration area is influenced by the vibration of the other vibration area is prevented in the frequency signals taken out from the two channels. Therefore, when the frequencies F1', F2' are obtained from these frequency signals as the time-series data and the time-series data of the difference between these frequencies is calculated, an error factor is removed, which enables the sensing instrument 5 to output the highly reliable measurement result.

Figure 9:
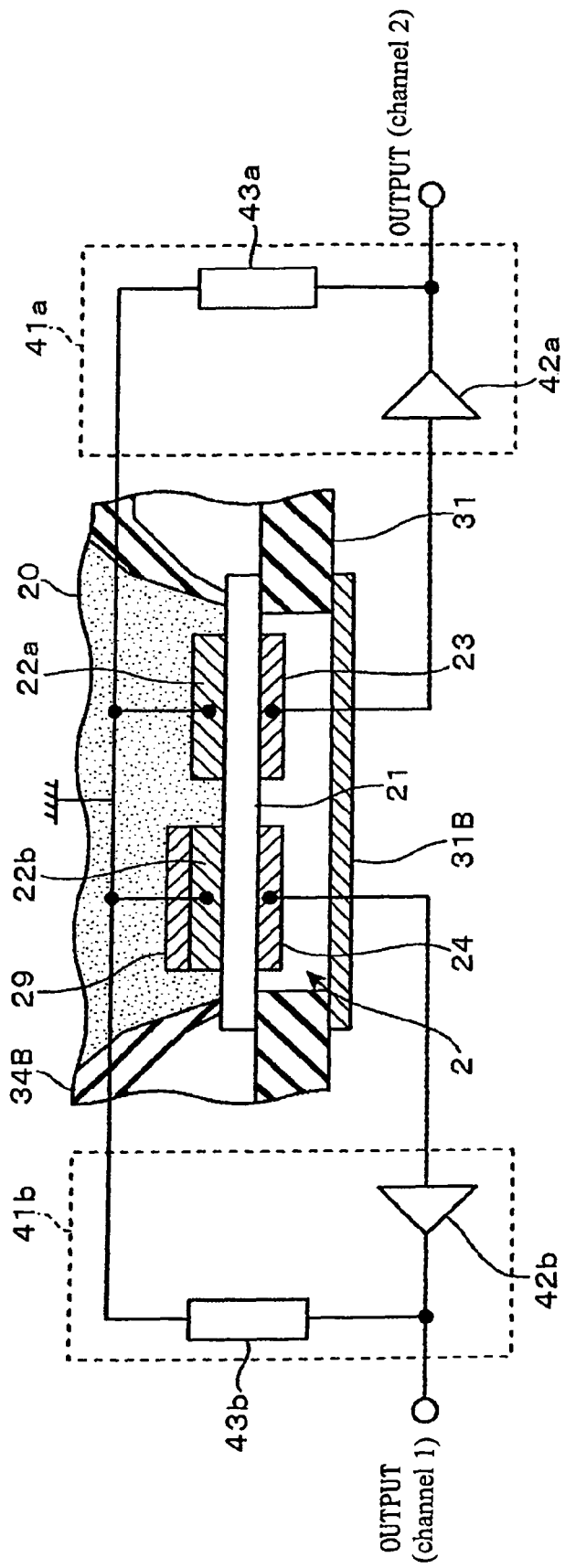
FIG. 9 is a vertical sectional view of another quartz sensor.
Figure 11:
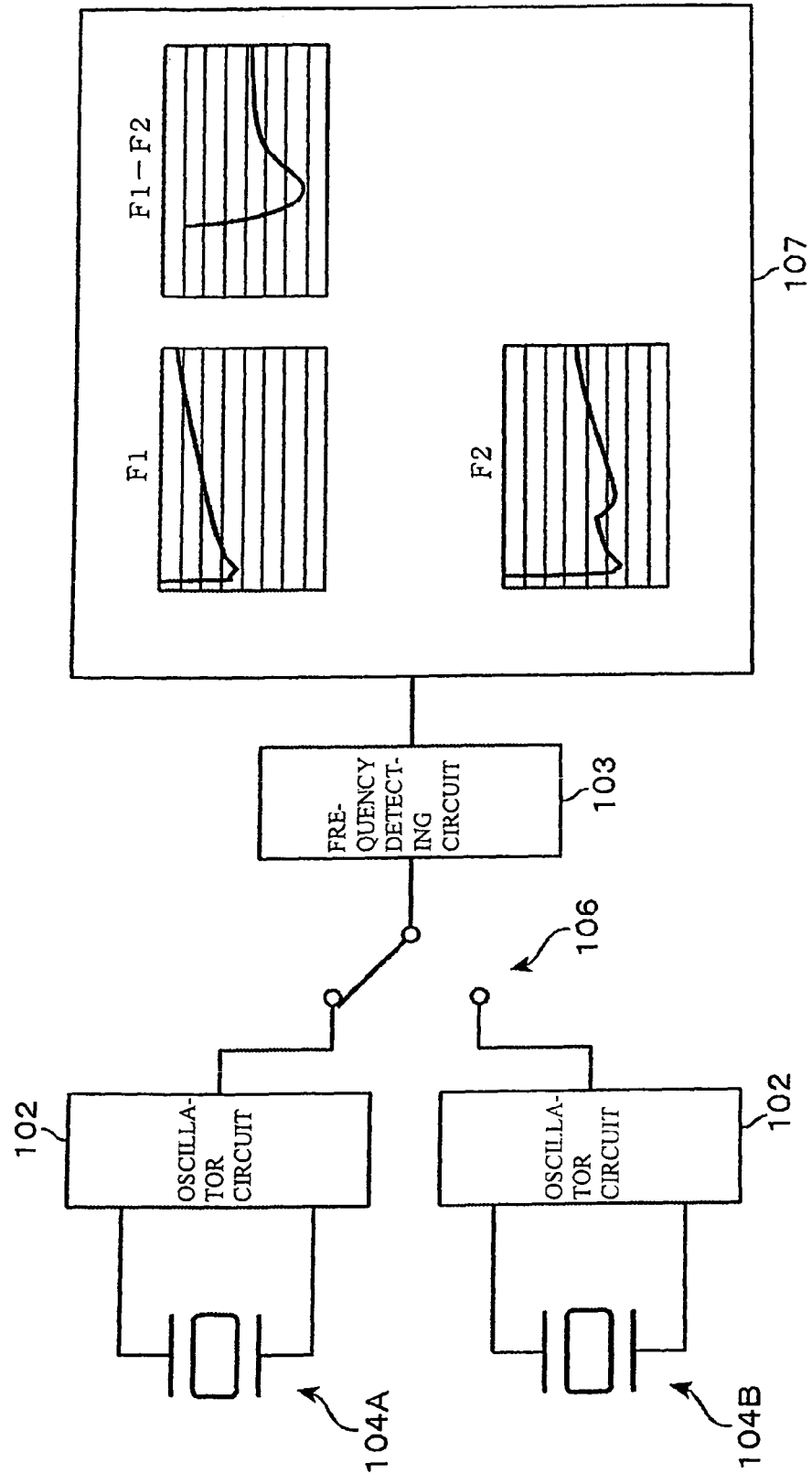
FIG. 11 is a block diagram of another conventional sensing instrument.
Figure 12:
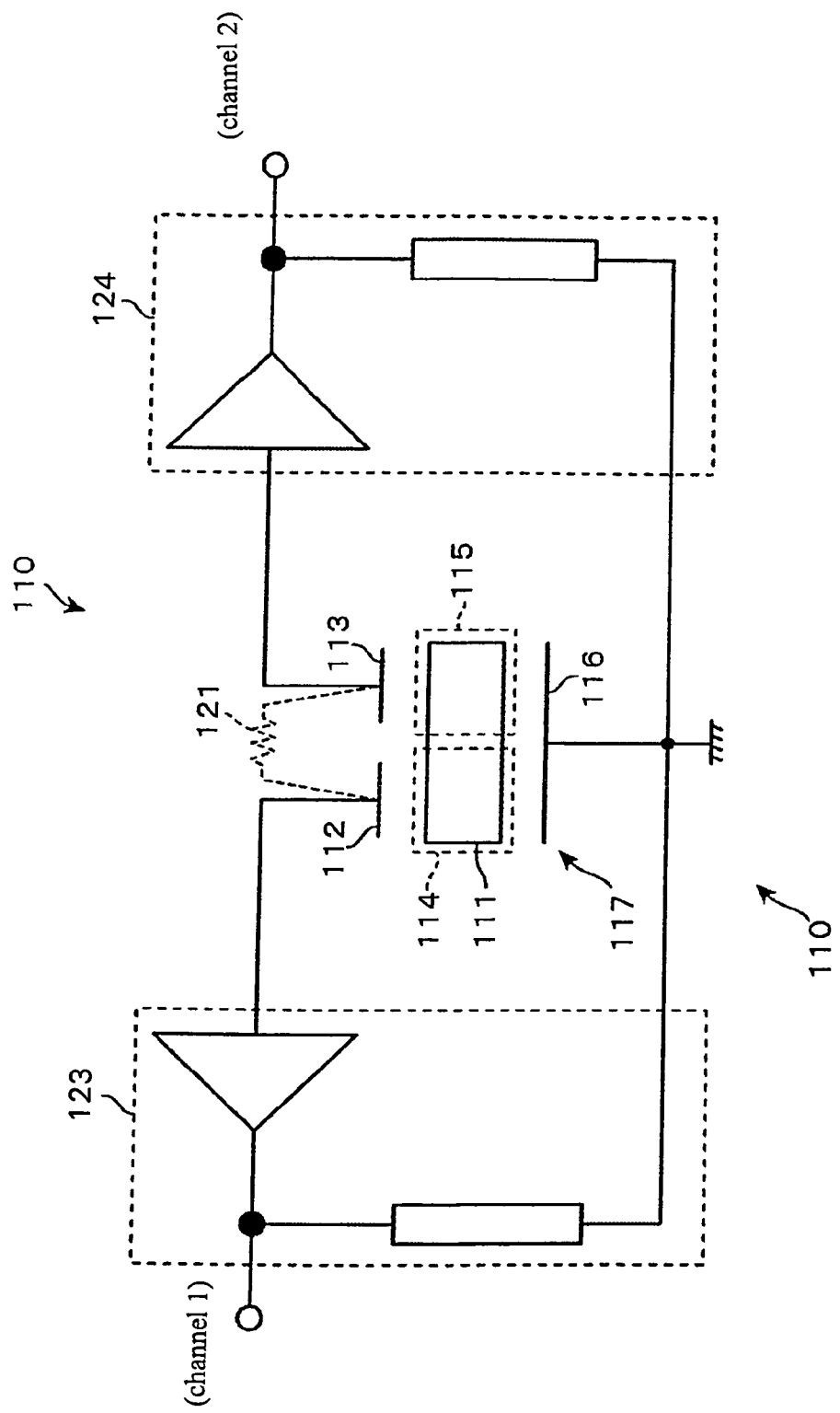
FIG. 12 is a circuit diagram of a conventional quartz oscillator circuit.
Figure 13:
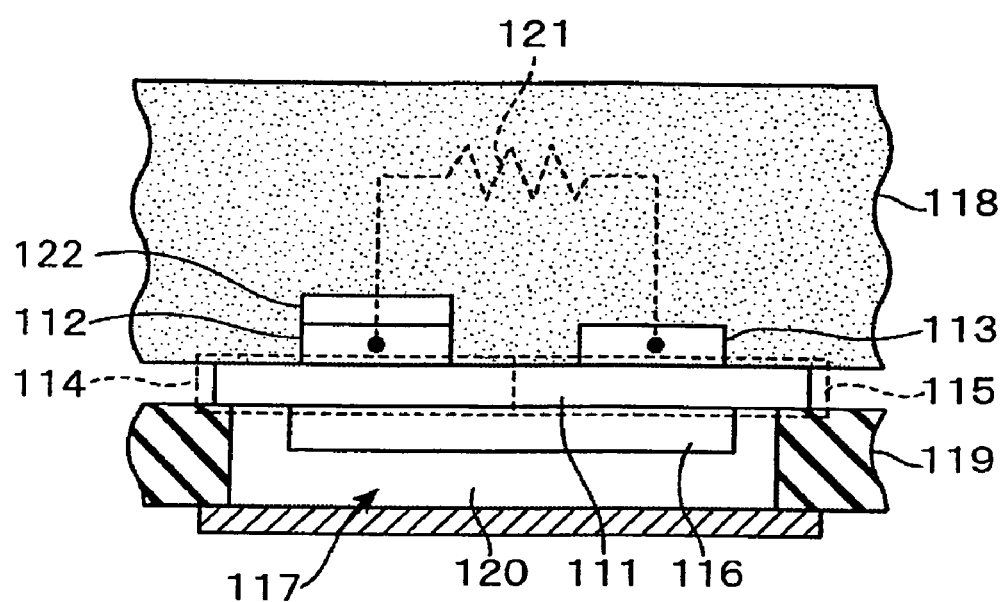
FIG. 13 is a side view of a quartz resonator included in the quartz oscillator circuit.
Figure 14:
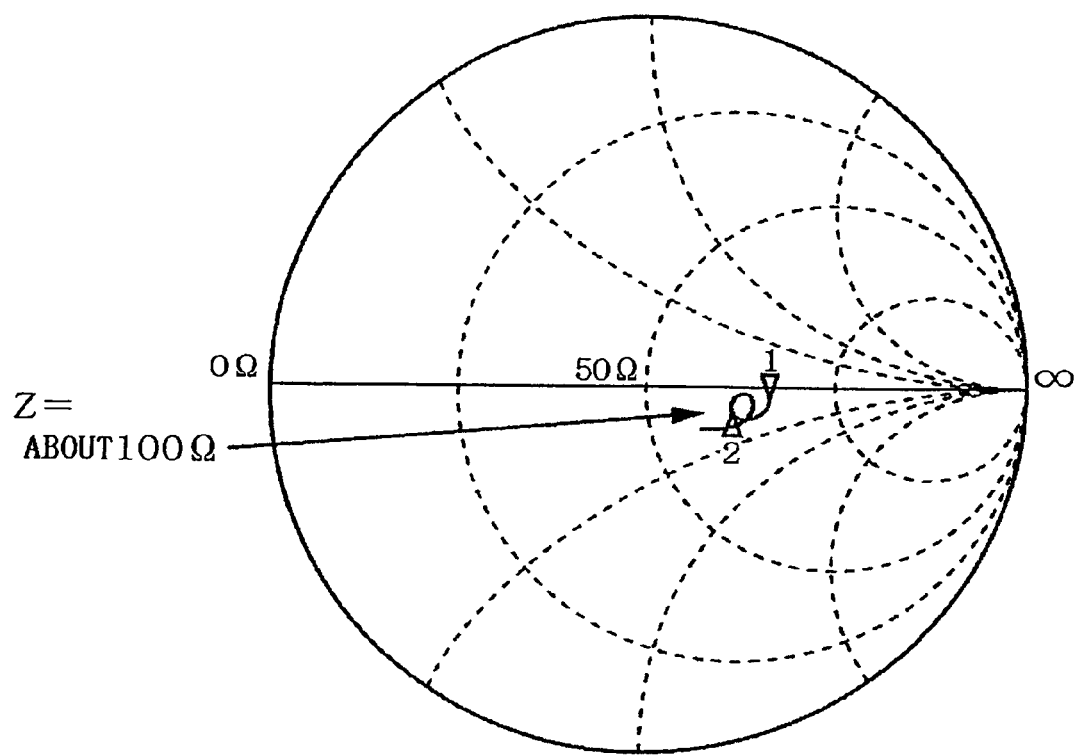
FIG. 14 is an explanatory chart showing impedance of the quartz resonator.

Incidentally, a common electrode which is divided and thus is not physically one sheet is called as the common electrode, provided that the divided electrodes are formed on one surface side of the quartz piece and are equal in potential, since there is no influence of the coupling between the divided electrodes due to the impedance. For example, as shown in FIG. 9 as another example, two electrodes 22a, 22b formed apart from each other on the front surface of the quartz piece 21 are grounded. Such electrodes 22a, 22b are also included in the common electrode. This embodiment can also provide the same effects as those of the above-described embodiment.

What is claimed is:

1. A piezoelectric sensor sensing a substance to be sensed in a sample fluid based on a change in natural frequency of a piezoelectric piece by making an adsorption layer formed on an electrode provided on the piezoelectric piece adsorb the substance to be sensed, the piezoelectric sensor comprising:
   a first electrode for measurement and a second electrode for reference provided apart from each other on one surface side of the piezoelectric piece;
   a common electrode provided on an opposite surface side of the piezoelectric piece commonly for said first electrode and said second electrode to face said first electrode and said second electrode;
   an adsorption layer formed on an area, of said common electrode, to which said first electrode is faced across the piezoelectric piece, to adsorb the substance to be sensed; and
   connecting mutually the area of said common electrode to which said first electrode is faced across the piezoelectric piece and an area of said common electrode to which said second electrode is faced across the piezoelectric piece electrically so that these areas are same electric potential.

2. The piezoelectric sensor according to claim 1, further comprising a support member supporting the piezoelectric piece, wherein
   said first electrode and said second electrode are located in a closed space formed by a recessed portion of said support member.

3. A sensing instrument comprising:
   the piezoelectric sensor according to claim 2;
   a first oscillator circuit connected between the first electrode and the common electrode to vibrate a vibration area between the first electrode and the common electrode in the piezoelectric piece; and
   a second oscillator circuit connected between the second electrode and the common electrode to vibrate a vibration area between the second electrode and the common electrode of the piezoelectric piece, wherein
   the common electrode is grounded.

4. A sensing instrument comprising:

the piezoelectric sensor according to claim 1;

a first oscillator circuit connected between the first electrode and the common electrode to vibrate a vibration area between the first electrode and the common electrode in the piezoelectric piece; and a second oscillator circuit connected between the second electrode and the common electrode to vibrate a vibration area between the second electrode and the common electrode of the piezoelectric piece, wherein the common electrode is grounded.

* * * * *